(12) United States Patent
Dar et al.

(10) Patent No.: US 6,620,255 B1
(45) Date of Patent: Sep. 16, 2003

(54) ADAPTABLE ULTRASONIC FIBER OPTIC CLEANING METHODS

(75) Inventors: Iqbal Mahmud Dar, Odenton, MD (US); Mila Obradovic, Silver Spring, MD (US)

(73) Assignee: Ciena Corporation, Linthicum, MD (US)

(*) Notice: Subject to any disclaimer, the term of this patent is extended or adjusted under 35 U.S.C. 154(b) by 0 days.

(21) Appl. No.: 09/274,901

(22) Filed: Mar. 23, 1999

(51) Int. Cl.[7] ................................................. B08B 3/12
(52) U.S. Cl. ........................................... 134/1; 134/184
(58) Field of Search ....................................... 134/1, 184

(56) References Cited

U.S. PATENT DOCUMENTS 4,035,210 A * 7/1977 Ohyoshi et al. ............... 134/3
6,085,763 A * 7/2000 Esmaeili et al. ............ 134/184

* cited by examiner

Primary Examiner—Randy Gulakowski
Assistant Examiner—Saeed Chaudhry
(74) Attorney, Agent, or Firm—Susan S. Morse; Michael R. Cammarata

(57) ABSTRACT

A frequency of an ultrasonic cleaner for cleaning an optical fiber can be varied, thereby facilitating removal of particles of various sizes. The control of the varying may be predetermined or may be closed loop. The control may also alter the duration of the application of the frequency. A container which insures a set position of the fiber and/or immersion of the fiber in a cleaning solution may be employed. The sizes of particles on the fiber to be cleaned may be determined and parameters for cleaning may be selected in accordance with the determined sizes.

17 Claims, 4 Drawing Sheets

ADAPTABLE ULTRASONIC FIBER OPTIC CLEANING METHODS

BACKGROUND OF THE INVENTION

1. Field of the Invention

The present invention is directed to an adaptable system and method for cleaning an optical fiber. More particularly, the present invention is directed to a tunable ultrasonic fiber optic cleaner and method.

2. Description of Related Art

When performing various types of optical assembly processing, such as fusion splicing, connecterizing, etc., on an optical fiber, the optical fiber, which is typically surrounded by a protective coating, must be stripped so that only the core and cladding of the optical fiber remain. In order to insure proper processing of the fiber, the fiber must be clean.

One method for cleaning the fiber involves using a solution, such as alcohol, acetone, or water, manually dipping the fiber into the solution and wiping the fiber clean. While this is satisfactory for some types of optical assembly processes, when performing other types, e.g., fusion splicing, it is extremely important that the fiber be clean in order to maintain the losses in the fiber at an acceptable level.

Therefore, an ultrasonic cleaner is used. The optical fiber is dipped in a solution and a set ultrasound frequency resonates in the solution. Standing waves develop which hit the fiber and cause it to vibrate. This vibration further aids the removal of particles from the fiber.

However, the ultrasonic cleaner of a set frequency does not remove all sizes of particles. Further, only manual adjustment of cleaning time is available on the fixed frequency ultrasonic cleaners. These cleaners do not readily allow automation of the cleaning process.

SUMMARY OF THE INVENTION

The present invention is therefore directed to a system of cleaning optical fibers and which substantially overcomes one or more of the problems due to the limitations and disadvantages of the related art.

It is an object of the present invention to provide an ultrasonic cleaner having a variable frequency for removing particles of different sizes from optical fibers.

It is another object of the present invention to provide closed loop control for cleaning optical fibers, preferably using a variable frequency ultrasonic cleaner.

It is further an object of the present invention to provide a container which allows for consistent placement of the fiber and/or insures immersion of the fiber in the solution.

At least one of the above and other objects may be realized by providing a system for cleaning an optical fiber including: a container for holding a solution and receiving the optical fiber, an ultrasonic generator generating ultrasonic frequencies, an ultrasonic transducer attached to the container and receiving frequencies from the ultrasonic generator, and a control for varying a frequency output by the ultrasonic generator.

Preferably, the container has notches in sides thereof for holding the optical fiber. Preferably, the container has levers on sides thereof for immersing the optical fiber in the solution in the container. The ultrasonic transducer is preferably a piezoelectric crystal. The control may further control a duration for which the frequency is generated.

Preferably, the system includes a sensing system which generates an image of the fiber. Preferably, a microprocessor receives the image of the fiber from the sensing system, the microprocessor determining sizes of particles on the fiber and setting a frequency of the ultrasonic generator in accordance with particle size. Preferably, the sensing system is constructed to capture an entire image of the fiber. The sensing system may be a camera system.

At least one of the above and other objects may be realized by providing a method of cleaning an optical fiber including: immersing the optical fiber in a solution, generating ultrasonic waves in the solution, and varying a frequency of the ultrasonic waves.

A duration for which a given frequency is generated may be controlled. The sizes of particles on the optical fiber may be determined and the varying of the frequency may be in accordance with sizes of particles on the optical fiber. The immersing may include exerting pressure on the optical fiber when the optical fiber is in position to be cleaned. The immersing may include positioning the optical fiber at a predetermined location.

At least one of the above and other objects may be realized by providing a container for use in cleaning an optical fiber including: a cup for holding solution, and a pair of levers on opposite sides of the cup, the pair of levers exerting pressure on the fiber when in a down position to immerse a portion of the optical fiber to be cleaned in the solution.

The container may further include notches in opposite sides of the cup which receive the optical fiber when the levers are in the down position. A cross bar connecting the pair of levers to allow simultaneous movement of the levers may be provided. A valve biasing the levers in an up position may be included.

At least one of the above and other objects may be realized by providing a method of controlling a process of cleaning an optical fiber including: determining a size of a particle on a fiber; and selecting a cleaning parameter to be applied to the fiber in accordance with the particle size.

The determining may include imaging the fiber. The process of cleaning may be an ultrasonic frequency process and the selecting may include selecting a frequency of the ultrasonic frequency process to be applied. The determining may determine a range of sizes and the selecting may select a range of frequencies in accordance with the range of sizes. The selecting may further include selecting a duration for which a selected frequency is to be applied.

While the present invention is described herein with reference to illustrative embodiments for particular applications, it should be understood that the present invention is not limited thereto. Those having ordinary skill in the art and access to the teachings provided herein will recognize additional modifications, applications, and embodiments within the scope thereof and additional fields in which the invention would be of significant utility without undue experimentation.

BRIEF DESCRIPTION OF THE DRAWINGS

The foregoing and other objects, aspects and advantages will be described with reference to the drawings, in which.

DETAILED DESCRIPTION OF PREFERRED EMBODIMENTS

According to the present invention, by altering a frequency of an ultrasonic cleaner in accordance with a size of particle remaining on a fiber to be cleaned, the fiber may be effectively cleaned to reduce the number of particles of a particular size to an acceptable level. The automatic feedback control of cleaning in accordance with the present invention allows the cleaning to be more expeditious, i.e., targeted to the exact particle size of interest remaining, while minimizing the application time of the cleaning agitation.

Figure 1:
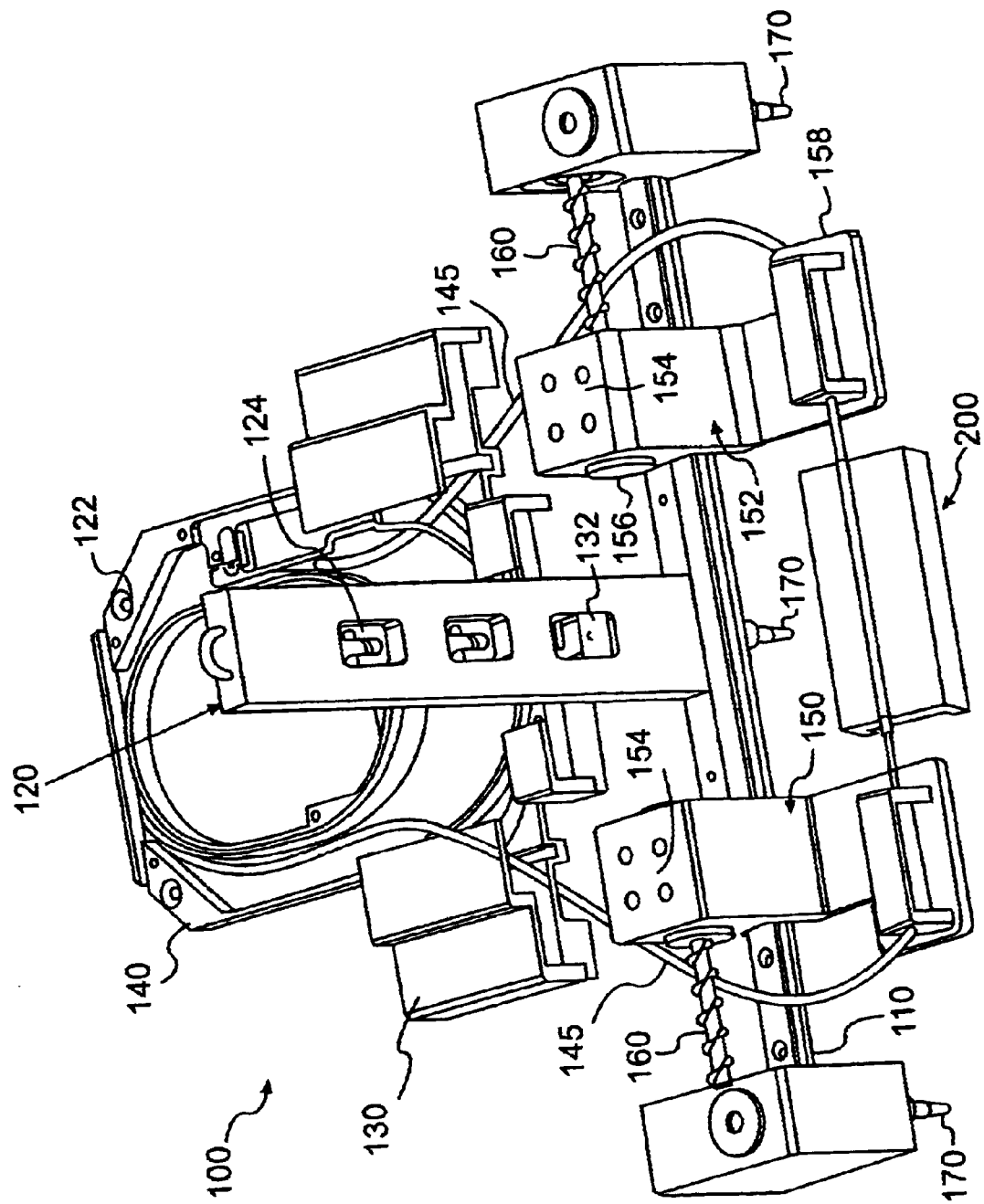
FIG. 1 is a perspective view of a metrology frame positioned with a cleaning system of the present invention.

When the cleaning of an optical fiber is part of an overall optical assembly process, the fiber may advantageously be moved through the various processing stages using a metrology frame 100 as shown in FIG. 1. The discussion of the metrology frame is only provided for completeness. Any known manner of immersing a fiber in a solution may be employed. A detailed discussion of the metrology frame 100 may be found in the commonly assigned, co-pending U.S. application Ser. No. 09/017,327 entitled "Optical Fiber Precision Handling Tool" filed Feb. 2, 1998, which is hereby incorporated by reference in its entirety for all purposes.

Referring to FIG. 1, the metrology frame 100 is used to hold, transport and align the optical fibers to be connected, and the fiber cassettes from which the optical fibers extend, during an optical fiber interconnection process. The metrology frame 100 includes an elongated lateral rail 110 serving as the attachment point for the majority of the components of the frame. A vertical support member 120 extends from an upper surface of the rail 110. The vertical support member 120 contains an attachment or end effector device 122 to allow a robot or gantry system to pick-up and transport the entire metrology frame 100 between the various steps of the optical assembly process. Since the frame 100 will be transported via the end effector 122, it is preferable to provide the vertical support 120 at a central location on the rail 110 to ensure the frame 100 is balanced during the transfer procedures.

The vertical support member 120 includes a plurality of vertically spaced attachment devices 124. A fiber cassette holder 130 includes a projection 132 that contacts and rests on the attachment device 124 to detachably attach the fiber cassette holder 130 to the vertical support member 120 in a substantially horizontal orientation with reference to the vertical support member 120. As shown in FIG. 1, the attachment device 124 is a projecting support bracket. Of course, one of ordinary skill in the art would understand that within the scope of the present invention, many different types of attachment devices may be used to detachably attach the fiber cassette holder 130 to the vertical support member 120. The attachment device chosen should provide a secure fit when the fiber cassette holder 130 and the vertical support member 120 are attached, but still provide the capability for easy insertion and removal.

A pair of aligning brackets 150 and 152 are provided on either side of the vertical support 120. The flange portion 155 of each of the brackets 150, 152 includes an aligning device 158 to align and secure the optical fibers during the interconnecting processes. A vertical portion 154 of each of the brackets 150, 152 contains a threaded lateral opening 156. The opening 156 is threaded to accommodate a lead screw 160 for moving the brackets 150, 152 laterally along the rail 110. Guide pins 170 position and anchor the metrology frame 100 on a planar surface.

As shown in FIG. 1, the optical fibers 145 from the fiber cassette 140 are passed through the aligning devices 158. Note that the aligning devices 158 in FIG. 1 are represented as cube-shaped devices for ease of illustration. However, it is understood that any number of conventional or custom aligning mechanisms may be incorporated into the metrology frame 100 of the present invention. As shown in FIG. 1 for example, after the optical fiber 145 is secured by the aligning devices 158, it is in position to undergo the various steps of the fusion or connecterization process between the respective brackets 150, 152, including cleaning. When used in the cleaning process, the metrology frame 100 supplies the fiber 145 to a container 200, discussed in detail below.

Figure 2A:
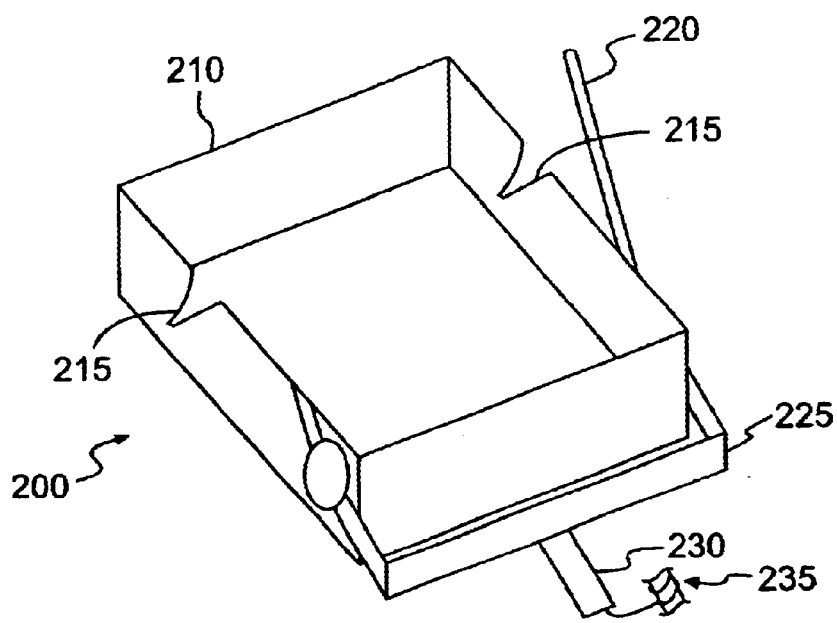
FIG. 2A is a perspective view of a container in accordance with the present invention in a transferring position.
Figure 2B:
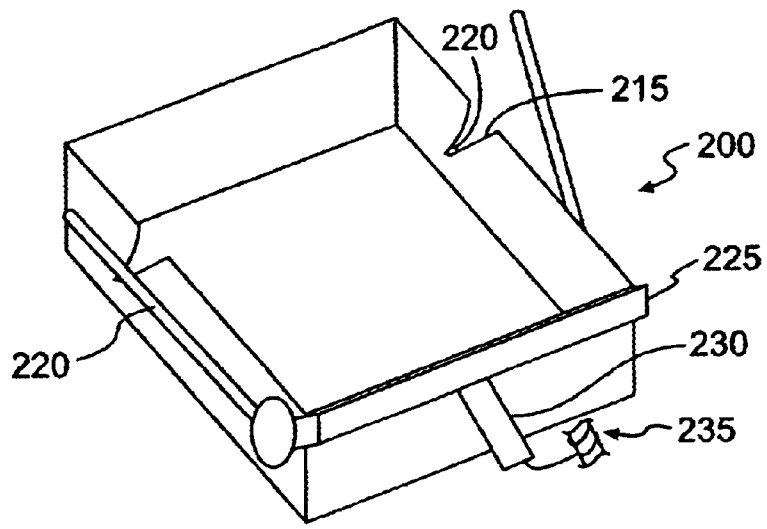
FIG. 2B is a perspective view of a container in accordance with the present invention in a cleaning position.

A container 200 for use in the cleaning process of the present invention is shown in FIGS. 2A and 2B. A cup 210 for containing solution to be used in the cleaning process preferably includes notches 215 for receiving the fiber to be cleaned therein. The presence of these notches 215 allows for accurate control of the location of the fiber in a transverse direction. The notches 215 are preferably tapered to the bottom thereof to accommodate fibers to be cleaned while not leaking solution therein. Any known solution for cleaning fibers may be used.

The container 200 also preferably includes a pair of levers 220, which may be connected together by a cross bar 225. The cross bar 225 allows the levers 220 to be raised and lowered simultaneously. As shown in FIGS. 2A and 2B, the cross bar 225 may have an arm 230 attached thereto for raising and lowering the cross bar 225, and hence the levers. The movement of the arm 230 is controlled by a solenoid valve 235. The arm preferably moves through a slot provided in a planar surface on which the container 200 is mounted.

The levers 220 are preferably biased in an up or raised position as shown in FIG. 2A. In the up position, a fiber may be transferred to and from the container 200. When the solenoid valve 235 is closed, the cross bar 225 is lifted, moving the levers 220 into the down position shown in FIG. 2B. When in the down position, the levers 220 force the fiber into the solution, overcoming surface tension that may prevent the fiber from dipping into the liquid. When cleaning is complete, the solenoid valve 235 is reopened and the levers 220 return to the up position shown in FIG. 2A.

When the cleaning solution to be employed is susceptible to rapid evaporation, it may be advantageous not to employ the notches 215, which, by increasing the exposed surface area of the solution, may serve to increase the evaporation rate, requiring replenishment of the solution for proper operation. When the notches 215 are not used, the fiber must be of a sufficient length so that it can withstand the bend radius imposed upon it by the application of the levers 220. For typical fibers, the width of the container 200 should be such that only at least a two inch radius of curvature is imposed on the fiber. Since only the ends of the fiber are stripped, the portion of fiber to be cleaned is still completely immersed even without the notches 215.

Figure 3:
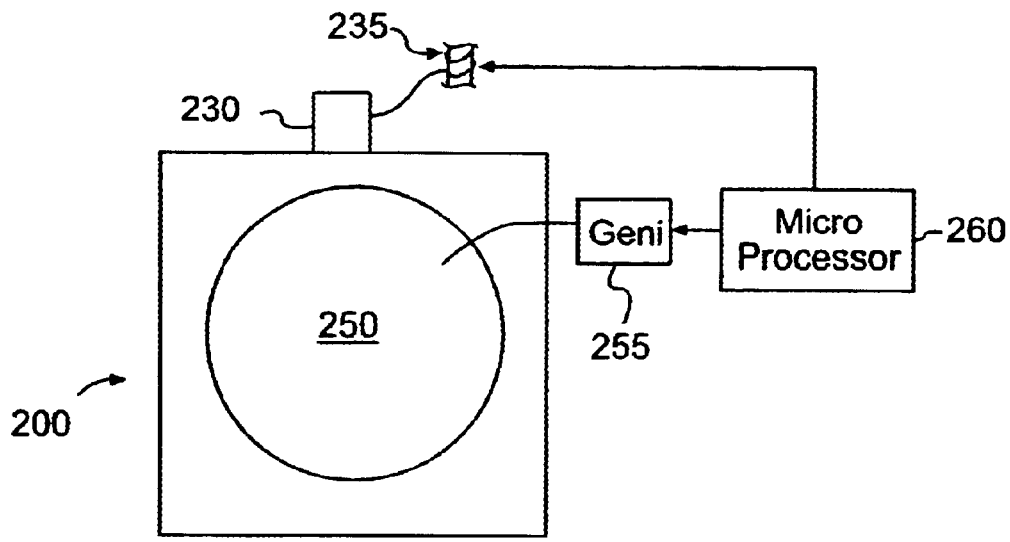
FIG. 3 is a bottom view of the container in accordance with the present invention with a schematic of a controller.

FIG. 3 is a bottom view of the container 200. As can be seen therein, an ultrasonic transducer 250, preferably a piezoelectric crystal, is provided on the bottom of the container 200. Such a transducer 250 converts an input frequency from an ultrasonic generator 255 into mechanical oscillations. These oscillations in turn create waves in the solution in the container 200. The frequency of the waves in the solution depends upon the size of the container 200, the volume of the solution and the type of solution. The frequency experienced by the fiber also depends on its location in the container 200.

In conventional systems, the ultrasonic frequency generated is 30 KHz, which is successful in removing particles on the order of 3 microns in size. While exposing the fiber to a long enough duration of this frequency will remove larger particles, the amount of energy input, and hence the stress endured by the fiber, is unnecessarily large. Further, prolonged application of this frequency does not remove particles which are smaller than on the order of 3 microns in size. An aspect of the present invention is directed to appreciating that the size of the particles removed by the solution oscillating at a particular frequency is a function of that frequency. Higher frequencies are needed to remove smaller particles and lower frequencies are needed to remove larger particles. Therefore, by varying the frequency, a range of particle sizes may be removed, while minimizing the stress to which the fiber is subjected. For example, by varying the frequency between 0 and 80 KHz, particle sizes down to 0.5 microns can be removed from the fiber.

While the ultrasonic frequency generator 255 may be manually controlled, a microprocessor 260 is preferably provided for controlling the frequency to be generated by the ultrasonic generator 255. The control may be a predetermined varying of frequencies for set time periods, a database of predetermined frequencies and durations for particular fibers, a manually input schedule, or a closed loop control discussed below. As noted above, the parameters are functions of the fibers being cleaned, the solution being used, the container being used and the location of the fiber in the container, as well as a desired level of cleanliness. Calibrations may be performed to optimize the parameters. Since the energy seen by the fiber is affected by the location of the fiber in the solution, the use of the notches 215, shown in FIGS. 2A and 2B, which accurately positions the fiber, is particularly advantageous.

Also, as shown in FIG. 3, the operation of the solenoid valve 235 may be controlled by the microprocessor 260. The closing of the solenoid valve 235 may be triggered by a start command input by a user or automatically when the microprocessor 260 determines the fiber is in position.

Closed loop control of the cleaning process of the present invention may be realized by inspecting the fiber to determine the size(s) of any particles on the fiber. Such closed loop control may be realized, for example, by imaging the fiber, preferably an entire circumference of the fiber. Typically, when the fiber is cylindrical, capture of the entire image will require two sensing devices in order to view the entire circumference of the fiber. These two sensing devices may be provided in any configuration which will allow them to image complementary portions of the fiber. For example, in the most direct approach, the sensing devices may be arranged rotated by 180° relative to one another. Alternatively, the image of the fiber may be directed to respective sensing devices using mirrors or other path altering devices appropriate for the wavelengths to be monitored. Typically, the image will be in the visible range, but may be in other ranges, such as the infrared range.

Figure 4:
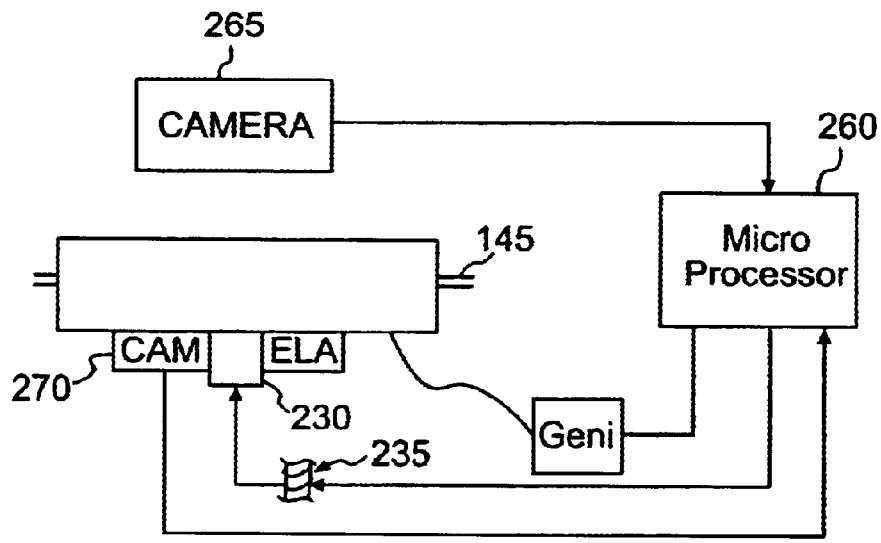
FIG. 4 is a side view of the container in accordance with the present invention with a schematic of a closed loop controller.

An example of such a configuration employing cameras as the sensing devices is shown in FIG. 4, in which a top camera 265 images a top of the fiber 145 being cleaned and a bottom camera 270 images a bottom of the fiber. Assuming the fiber is cylindrical, these two images will form a complete 360° image of the fiber. From this image, the size of any particles may be determined. Preferably, the fiber 145 is lifted out of the solution by the levers 220 to reduce noise. When the fiber is lifted out, it is preferable to use sensing devices located in positions orthogonal to those shown in FIG. 4, since the sensing is then no longer through the solution for either sensing device.

When using the specific closed loop control as shown in FIG. 4, the container 200 is transparent to the wavelengths of the image to be monitored. The frequency and duration of the pulse needed to remove these particles may be retrieved from a lookup table, and the ultrasonic generator 255 may be controlled in accordance with these retrieved parameters. Such a lookup table may be generated experimentally for a given solution and container configuration.

It is particularly important to minimize the amount of time the higher frequencies are applied, since these higher frequencies subject the fiber 145 to more stress. Therefore, by determining the particle size(s) on the fiber, the frequency and duration may be matched to the cleaning requirement of the fiber. Thus, the fiber may be cleaned of a range of particle sizes while minimizing an amount of energy stressing the fiber. The imaging of the fiber may also be used to select parameters for optimizing the cleaning process.

Figure 5:
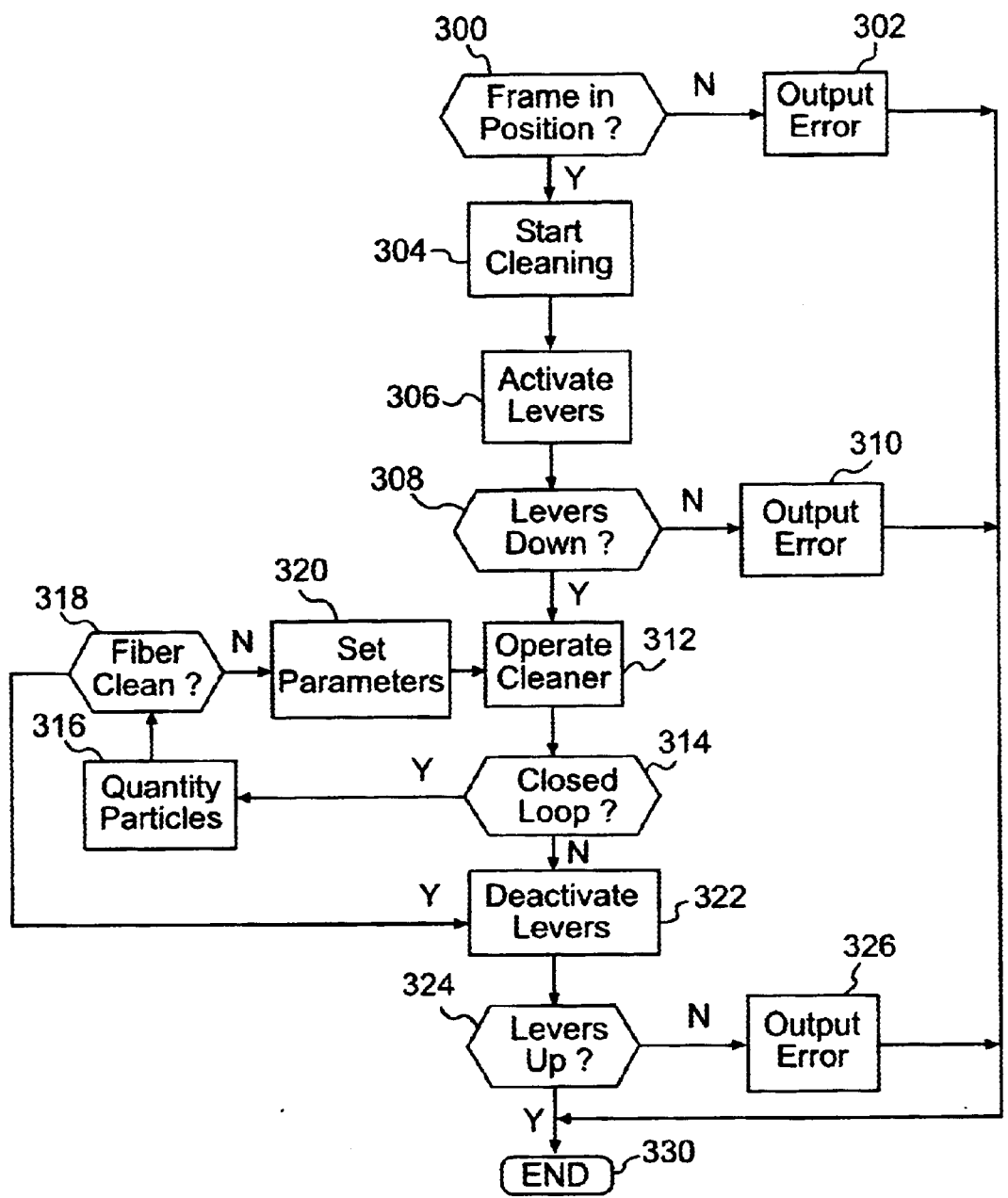
FIG. 5 is a flow chart of the automated cleaning in accordance with the present invention.

A flow chart illustrating the cleaning process of the present invention in shown in FIG. 5. While this flow chart illustrates the use of the metrology frame 100 and the container 200, the operation of the cleaner alone may be employed without these steps.

In step 300, whether or not the metrology frame is in position for cleaning is checked. If it is not, step 302 outputs an error signal. If it is, then step 304 starts the cleaning process. The cleaning process may be started manually be a user, or may automatically start when the frame is in position.

Step 306 activates the levers and step 308 determines whether the levers are in the down position, shown in FIG. 2B. If not, step 310 outputs an error signal. If the levers are down, than the cleaner is operated by step 312. If the control of the cleaner is an open loop, then the operation of the cleaner is self-contained, i.e., no other inputs are needed. If the control of the cleaner is a closed loop, as determined in step 314, further inputs are needed for the completion of operation of the cleaner.

In the closed loop control, step 316 quantifies the particles remaining on the fiber. If there are few enough particles or if the particles are below a certain size in accordance with a desired level of cleanliness, step 318 will determine that the fiber is clean. If the fiber is not found to be clean in step 318, step 320 sets parameters, i.e., frequency and duration, for the cleaner in accordance with the particle size(s) on the fiber.

Once the operation of the cleaner is complete, step 322 deactivates the levers. Step 324 determines whether the levers are in the up position, shown in FIG. 2A, for allowing proper removal of the fiber. If not, step 326 outputs an error signal. Step 330 ends the process.

Thus, in accordance with the present invention, a range of particles may be removed from a fiber by varying a frequency of an ultrasound cleaner. The control of the frequency varying may be manual, predetermined or provided by a closed loop. The parameters of the cleaning process may be optimized. A container for ensuring consistent placement of the fiber and/or immersion of the fiber in the solution may be employed.

While the present invention is described herein with reference to illustrative embodiments for particular applications, it should be understood that the present invention is not limited thereto. For example, while the inspection of the fiber has been disclosed as occurring at the same station as the cleaning, this inspection could take place at a remote location. For logistic reasons, it is typically simpler to inspect the fiber while leaving it at the cleaning station. Additionally, while closed loop control has only been discussed for ultrasonic frequency cleaning, the control of the cleaning in accordance with sizes of particles determined to be on the fiber being cleaned maybe used with other cleaning techniques. Those having ordinary skill in the art and access to the teachings provided herein will recognize additional modifications, applications, and embodiments within the scope thereof and additional fields in which the invention would be of significant utility without undue experimentation.

What is claimed is:

1. A method of cleaning an optical fiber, comprising:
   immersing the optical fiber in a solution;
   generating ultrasonic waves in the solution;
   determining at least one size of a particle contaminating a surface of the optical fiber by collecting image data of the optical fiber and processing the image data;
   varying a frequency of the ultrasonic waves generated by said generating step; and
   controlling said varying step according to the size of the particle determined by said determining step.

2. The method of claim 1,
   said controlling step controlling a duration time period for each frequency generated by said generating step according to the size of the particle determined by said determining step.

3. The method of claim 1, said determining step determining sizes of particles on the optical fiber and wherein said control step controls said varying of the frequency in accordance with sizes of particles on the optical fiber determined by said determining step.

4. The method of claim 1, wherein said immersing includes exerting pressure on the optical fiber when the optical fiber is in position to be cleaned.

5. The method of claim 1, wherein said immersing includes positioning the optical fiber at a predetermined location.

6. A method of controlling a process of cleaning an optical fiber comprising:
   determining a size of at least one particle on the optical fiber by collecting image data of the optical fiber and processing the image data; and
   selecting a cleaning parameter to be applied to the fiber in accordance with the particle size determined by said determining step.

7. The method of claim 6, wherein the process of cleaning is an ultrasonic frequency process and said selecting includes selecting a frequency of the ultrasonic frequency process to be applied.

8. The method of claim 7, wherein when said determining determines a range of sizes and said selecting selects a range of frequencies.

9. The method of claim 7, wherein said selecting further comprises selecting a duration for which a selected frequency is to be applied.

10. A method of cleaning an optical fiber, comprising:
    collecting a database of fiber cleaning information;
    immersing the optical fiber in a solution;
    generating ultrasonic waves in the solution to clean the optical fiber;
    determining a particle size of at least one particle on a surface of the optical fiber by obtaining image data of the optical fiber and processing the image data; and
    controlling said generating step according to the fiber cleaning information database collected by said collecting step and the particle size determined by said determining step.

11. The method of cleaning an optical fiber according to claim 10,
    said collecting step collecting fiber cleaning information including duration of ultrasonic frequency application information and particle size information.

12. The method of cleaning an optical fiber according to claim 10,
    said collecting step collecting fiber cleaning information including ultrasonic frequency information and particle size information.

13. The method of cleaning an optical fiber according to claim 10,
    said collecting step collecting fiber cleaning information including ultrasonic frequency information, duration of ultrasonic frequency application information, and particle size information.

14. The method of cleaning an optical fiber according to claim 10,
    said collecting step collecting fiber cleaning information including fiber information, solution information, container information, ultrasonic frequency information, duration of ultrasonic frequency application information, and particle size information.

15. The method of cleaning an optical fiber according to claim 10,
    said collecting step storing the database of fiber cleaning information in a look-up table; and
    said controlling step accessing the look-up table to control said generating step.

16. The method of cleaning an optical fiber according to claim 10, further comprising:
    performing a closed loop control of the fiber optic cleaning by iterating said determining and controlling steps until the optical fiber meets at least one cleanliness standard.

17. The method of cleaning an optical fiber according to claim 10,
    said determining step including imaging substantially an entire circumference of the optical fiber.

* * * * *